(12) United States Patent
Vacanti

(10) Patent No.: US 12,115,281 B2
(45) Date of Patent: Oct. 15, 2024

(54) SYSTEMS FOR AND METHODS FOR USING BIOMIMETIC STRUCTURES PROVIDING COMMUNICATION IN LIVING TISSUE

(71) Applicant: The General Hospital Corporation, Boston, MA (US)

(72) Inventor: Joseph P. Vacanti, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/068,168

(22) Filed: Dec. 19, 2022

(65) Prior Publication Data

US 2023/0372588 A1 Nov. 23, 2023

Related U.S. Application Data

(63) Continuation of application No. 15/752,508, filed as application No. PCT/US2016/044435 on Jul. 28, 2016, now Pat. No. 11,534,530.
(Continued)

(51) Int. Cl.
| | |
|---|---|
| *A61L 27/38* | (2006.01) |
| *A61F 2/06* | (2013.01) |
| *A61L 27/50* | (2006.01) |
| *A61L 27/52* | (2006.01) |
| *C12M 1/12* | (2006.01) |
| *C12M 3/00* | (2006.01) |
| *C12N 5/071* | (2010.01) |

(52) U.S. Cl.
CPC .......... *A61L 27/3808* (2013.01); *A61F 2/062* (2013.01); *A61L 27/507* (2013.01); *A61L 27/52* (2013.01); *C12M 21/08* (2013.01); *C12M 25/10* (2013.01); *C12M 25/14* (2013.01); *C12N 5/0671* (2013.01); *C12N 2533/50* (2013.01)

(58) Field of Classification Search
CPC ............ A61F 2/06–062; A61L 27/507; A61L 27/3804; A61L 27/3808; A61L 27/3834; C12M 25/10; C12M 25/14; C12M 21/08
See application file for complete search history.

(56) References Cited

U.S. PATENT DOCUMENTS

| 6,143,293 A | 11/2000 | Weiss et al. |
| 6,455,311 B1 | 9/2002 | Vacanti |

(Continued)

FOREIGN PATENT DOCUMENTS

| CN | 102076366 A | 5/2011 |
| CN | 202129066 U | 2/2012 |

(Continued)

OTHER PUBLICATIONS

Russian Federation, Patent Office of the, Office Action, Application No. 2018108802, Jan. 24, 2020.
(Continued)

*Primary Examiner* — Thaddeus B Cox
(74) *Attorney, Agent, or Firm* — Quarles & Brady LLP

(57) ABSTRACT

A platform for creating engineered tissues includes a vascular tube that defines a vascular diameter and is configured to receive vascular system seed cells, a non-vascular tube that defines a non-vascular tube diameter and is configured to receive organ system seed cells, and a barrier formed between the vascular tube and the non-vascular tube.

18 Claims, 5 Drawing Sheets

Related U.S. Application Data

(60) Provisional application No. 62/205,214, filed on Aug. 14, 2015.

(56) References Cited

U.S. PATENT DOCUMENTS

| | | | |
|---|---|---|---|
| 8,357,528 | B2 | 1/2013 | Vacanti et al. |
| 8,591,597 | B2 | 11/2013 | Hoganson et al. |
| 2002/0182241 | A1 | 12/2002 | Borenstein et al. |
| 2004/0137613 | A1* | 7/2004 | Vacanti ............... A61L 27/3817 |
| | | | 435/366 |
| 2006/0019326 | A1 | 1/2006 | Vacanti et al. |
| 2006/0136182 | A1 | 6/2006 | Vacanti et al. |
| 2007/0281353 | A1 | 12/2007 | Vacanti et al. |
| 2010/0057196 | A1* | 3/2010 | Pathak ..................... A61F 2/82 |
| | | | 623/1.42 |
| 2010/0098742 | A1 | 4/2010 | Vacanti et al. |
| 2010/0234678 | A1 | 9/2010 | Pryor et al. |
| 2011/0024346 | A1 | 2/2011 | Weinberg et al. |
| 2011/0250585 | A1 | 10/2011 | Ingber et al. |
| 2013/0030548 | A1 | 1/2013 | Ling |
| 2013/0164339 | A1 | 6/2013 | Murphy et al. |
| 2013/0196438 | A1 | 8/2013 | Chun et al. |
| 2014/0234953 | A1 | 8/2014 | Vacanti et al. |
| 2015/0050686 | A1 | 2/2015 | Sheth et al. |
| 2016/0271610 | A1 | 9/2016 | Foulds et al. |
| 2016/0287756 | A1 | 10/2016 | Lewis et al. |
| 2017/0252701 | A1 | 9/2017 | Nosrati |
| 2019/0358367 | A1 | 11/2019 | Vacanti et al. |

FOREIGN PATENT DOCUMENTS

| | | |
|---|---|---|
| JP | 2006341087 A | 12/2006 |
| NC | 20180013143 | 4/2018 |
| WO | 2014052835 A1 | 4/2014 |

OTHER PUBLICATIONS

Russian Federation, Patent Office of the, Search Report, Application No. 2018108802, Jan. 24, 2020.
Russian Federation, Patent Office of the, Official Action, Application No. 2018108802, Apr. 28, 2021, 8 pages.
Russian Federation, Patent Office of the, Notification, Application No. 2018108802, Feb. 25, 2022, 9 pages.
Russian, Federal Service for Intellectual Property, Decision to Grant, Report on Results of Examination, Application No. 2018108802, Oct. 10, 2022, 15 pages.
Sadovoy et al., Cellular Matrices (Scaffolds) for Bone Regeneration: State of the Art, Spinal Surgery, 2014, 2:79-86, With English Abstract.
Saudi Arabia Patent Office, Office Action, Application No. 518390931, Nov. 15, 2020, 9 pages.
Saudi Arabia Patent Office, Office Action, Application No. 518390931, Jun. 9, 2021, 5 pages.
Saudi Authority for Intellectual Property, Notice of Rejection, Application No. 518390931, Notice of Rejection, May 24, 2022, 7 pages [Includes brief summary of office action in English].
Singapore, Intellectual Property Office of, Search Report and Written Opinion, Application No. 11201801218R, Apr. 2, 2019, 11 pages.
Singapore, Intellectual Property Office of, Examination Report, Application No. 11201801218R, Jul. 15, 2020, 5 pages.
United Arab Emirates Ministry of Economy, Examination Report and Search Report, Application No. P6000247/18, Oct. 20, 2021, 14 pages.
Vietnam, Intellectual Property Office of, Office Action, Application No. 1-2018-01018, Jun. 29, 2022, 4 pages.
Vietnam, Intellectual Property Office of, Office Action, Application No. 1-2018-01018, May 31, 2023, 4 pages.

Msconti et al., Towards Organ Printing: Engineering an Intra-Organ Branched Vascular Tree, Expert Opinion on Biological Therapy, 2010, 10(3):409-420.
Xiong et al., Jet-Based 3D Printing of Biological Constructs, Solid Freeform Fabrication Symposium, 2014 Proceedings, pp. 1069-1075.
Zein et al., Three-Dimensional Print of a Liver for Preoperative Planning in Living Donor Liver Transplantation, Liver Transplantation, 2013, 19(12):1304-1310.
African Regional Intellectual Property Organization (ARIPO), Examination Report, Application No. AP/P/2018/010529, Aug. 18, 2021, 5 pages.
An et al., Design and 3D Printing of Scaffolds and Tissues, Engineering, 2015, 1(2):261-268.
Australia IP, Examination Report No. 1, Application No. 2016307768, Oct. 21, 2021, 3 pages.
Brazil National Institute of Industrial Property, Report, Application No. BR112018002950-5, Jun. 16, 2020, 9 pages.
Brazil National Institute of Industrial Property, Written Opinion, Application No. BR112018002950-5, Jun. 22, 2021, 13 pages.
Brazil National Institute of Industrial Property, Rejection Decision, Application No. BR112018002950-5, Nov. 9, 2021, 13 pages.
Canadian Intellectual Property Office, Office Action, Application No. 2,995,578, Oct. 13, 2022, 4 pages.
Canadian Intellectual Property Office, Office Action, Application No. 2,995,578, Aug. 18, 2023, 3 pages.
China National Intellectual Property Administration, First Office Action and Search Report, Application No. 201680053081.9, Jan. 20, 2021, 16 pages.
China National Intellectual Property Administration, Second Office Action, Application No. 201680053081.9, Oct. 11, 2021, 9 pages.
China National Intellectual Property Administration, Third Office Action, Application No. 201680053081.9, Jan. 18, 2022, 8 pages.
China National Intellectual Property Administration, Decision on Rejection, Application No. 201680053081.9, Jul. 1, 2022, 11 pages.
China National Intellectual Property Administration, First Office Action, Application No. 202211268111.1, Jun. 7, 2023, 8 pages.
Colombia Patent Office, Office Action, Application No. NC2018/0002590, Jan. 22, 2020, 9 pages.
Colombia Patent Office, Office Action, Application No. NC2018/0002590, Feb. 2, 2021, 16 pages.
Colombia Patent Office, Office Action, Application No. NC2018/0002590, Oct. 29, 2021, 21 pages.
Columbia Patent Office, Office Action, Application No. NC2018/0002590, May 13, 2022, 22 pages.
Dhir et al., Novel Ex Vivo Model for Hands-On Teaching Of and Training in EUS-Guided Biliary Drainage: Creation of "Mumbai EUS" Stereolithography/3D Printing Bile Duct Prototype (with Videos), Gastrointestinal Endoscopy, 2015, 81 (2):440-446.
Egyptian Patent Office, Office Action, Application No. 277-2018, Jun. 22, 2021, 5 pages.
Egyptian Patent Office, Office Action, Application No. 277-2018, Nov. 17, 2021, 7 pages.
European Patent Office, Supplementary Partial European Search Report, Application No. 16837473.4, Mar. 1, 2019, 13 pages.
European Patent Office, Extended European Search Report, Application No. 16837473.4, Jun. 17, 2019, 10 pages.
European Patent Office, Communication, Application No. 16837473.4, Sep. 24, 2020, 4 pages.
Griffith et al., In Vitro Organogenesis of Liver Tissue, Annals of the New York Academy of Sciences, 1997, 831 (1):382-397.
Hasan et al., A Multilayered Microfluidic Blood Vessel-Like Structure, Biomed Microdevices, 2015, 17(5):88, 13 pages.
India, Intellectual Property, Examination Report, Application No. 201817009190, Oct. 7, 2021, 8 pages.
Indonesia Patent Office, Office Action, Application No. P00201801806, Aug. 31, 2020, 1 page.
Indonesia Patent Office, Second-Phased Substantive Examination Outcome, Application No. P00201801806, Jun. 9, 2021, 4 pages.
Israeli Patent Office, Office Action, Application No. 257528, Mar. 5, 2019, 5 pages.
Israeli Patent Office, Office Action, Application No. 257528, Sep. 19, 2020, 9 pages.

(56) References Cited

OTHER PUBLICATIONS

Israeli Patent Office, Office Action, Application No. 257528, Dec. 28, 2021, 7 pages.
Japan Patent Office, Notification of Reason for Refusal, Application No. 2018-527834, Sep. 15, 2020, 9 pages.
Japan Patent Office, Notification of Reason for Refusal, Application No. 2018-527834, Apr. 13, 2021, 4 pages.
Japan Patent Office, Decision of Refusal, Application No. 2018-527834, Jan. 25, 2022, 5 pages.
Japan Patent Office, Notification of Reason for Refusal, Application No. 2022-084389, Feb. 14, 2023, 6 pages.
Korean Intellectual Property Office, Notice of Preliminary Rejection, Application No. 10-2018-7007190, Mar. 8, 2023, 13 pages.
Krueger et al., Challenges in Lung Transplantation, Swiss Medical Weekly, 2011, 141:w13292, pp. 1-7.
Lectures on Human Anatomy, Part II, Internal Organs, Cardiovascular System, Second Edition, Vitebsk, VSMU, 2010, pp. 5-6 [Cited on p. 3 of Russian Patent Office dated Feb. 25, 2022].
Lu et al., Techniques for Fabrication and Construction of Three-Dimensional Scaffolds for Tissue Engineering, International Journal of Nenomedicine, 2013, 8:337-350.
Malaysia, Intellectual Property Corporation of, Substantive Examination Examiner's Report and Search Report, Application No. PI 2018000221, Jun. 20, 2022, 4 pages.
Malaysia, Intellectual Property Corporation of, Substantive Examination Clear Report, Application No. PI 2018000221, May 23, 2023, 1 page.
Mexican Patent Office, Office Action, Application No. MX/a/2018/001888, Sep. 17, 2021, 5 pages.
Mexican Patent Office, Official Action, Application No. MX/a/2018/001888, May 25, 2022, 5 pages [Includes brief summary of office action in English].
Mexican Patent Office, Official Action, Application No. MX/a/2018/001888, Dec. 13, 2022, 5 pages [Includes brief summary of office action in English].
Moreno et al., Post-Liver Transplantation Medical Complications, Annals of Hepatology, 2006, 5(2):77-85.
Murphy et al., 3D Bioprinting of Tissues and Organs, Nature Biotechnology, 2014, 32(8):773-785.
New Zealand Intellectual Property Office, Patent Examination Report 1, Application No. 740635, May 2, 2023, 4 pages.
New Zealand Intellectual Property Office, Patent Examination Report 1, Application No. 778521, May 2, 2023, 3 pages.
PCT International Search Report and Written Opinion, PCT/US2016/044435, Nov. 29, 2016, 14 pages.
PCT International Search Report and Written Opinion, PCT/US2019/034219, Aug. 16, 2019, 12 pages.
China National Intellectual Property Administration, Second Office Action, Application No. 202211268111.1, Dec. 15, 2023, 7 pages.

* cited by examiner

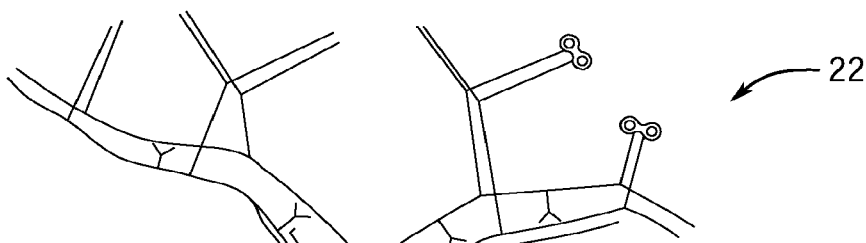
FIG. 1
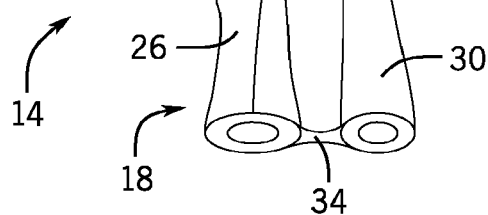
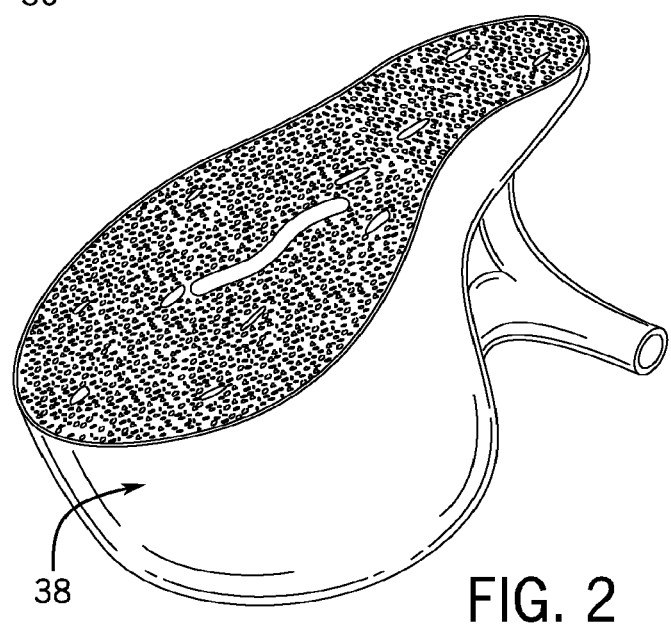
FIG. 2
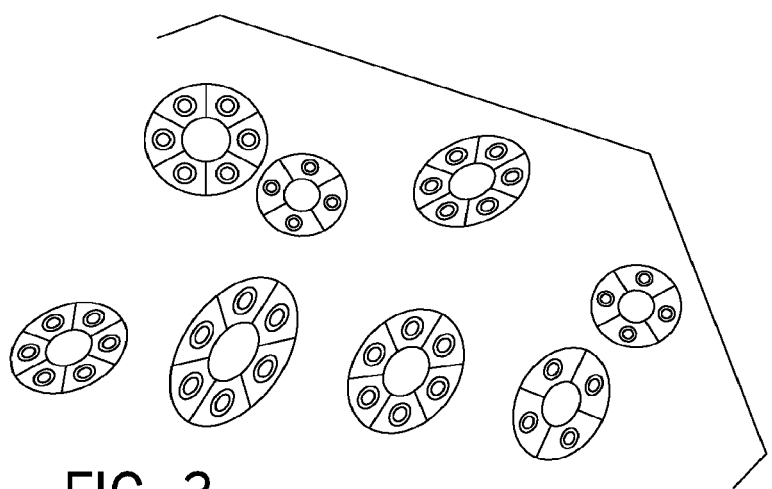
FIG. 3

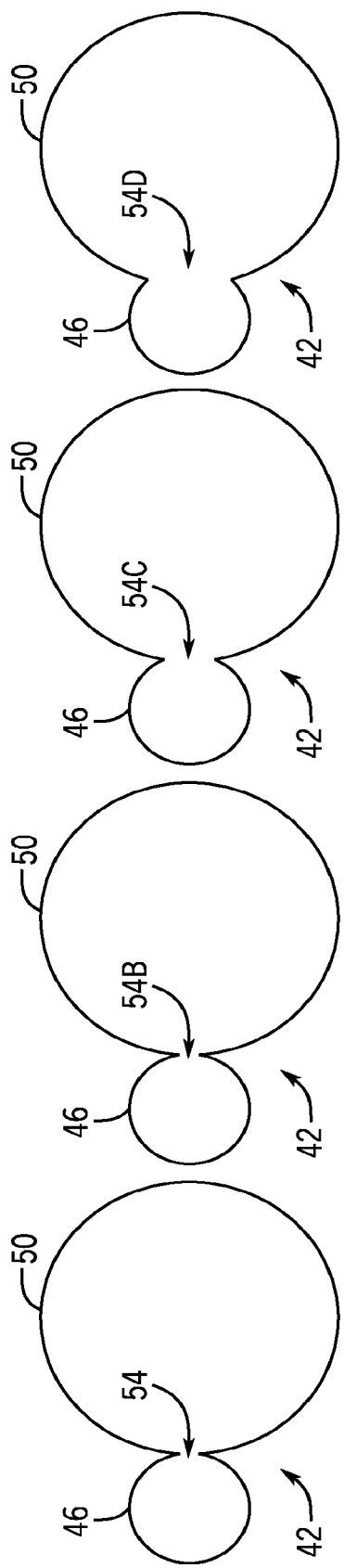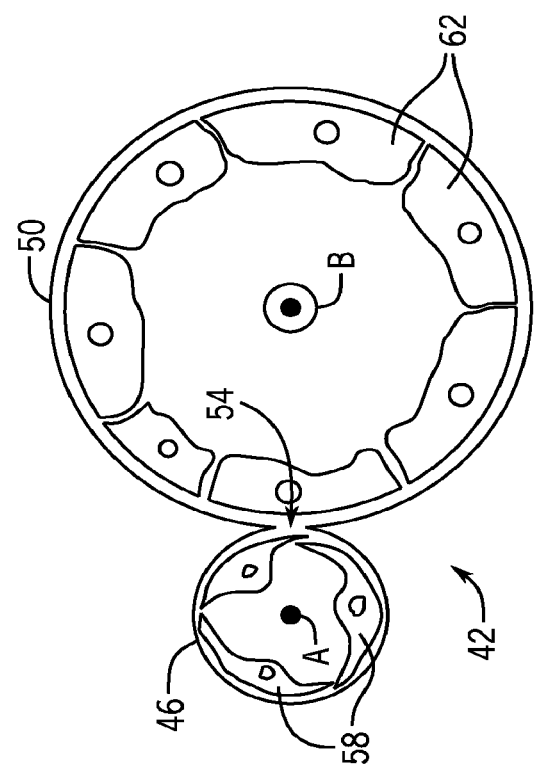

SYSTEMS FOR AND METHODS FOR USING BIOMIMETIC STRUCTURES PROVIDING COMMUNICATION IN LIVING TISSUE

CROSS REFERENCE TO RELATED APPLICATIONS

This application is a continuation of U.S. patent application Ser. No. 15/752,508 filed on Feb. 13, 2018, now U.S. Pat. No. 11,534,530, which is a U.S. National Phase of PCT Application No. PCT/US2016/044435 filed on Jul. 28, 2016, which is based on, claims priority to, and incorporates herein by reference in its entirety, U.S. Provisional Application No. 62/205,214 filed on Aug. 14, 2015, and entitled "SYSTEMS FOR AND METHODS FOR USING BIOMIMETIC STRUCTURES PROVIDING COMMUNICATION IN LIVING TISSUE."

BACKGROUND OF THE DISCLOSURE

Organ transplantation is a viable treatment for patients with end-stage organ disease. However, the number of patients is greater than the number of organ donors in the United States and worldwide. Patients awaiting liver, lung, and heart transplants often fail to receive an organ due to the long transplant waiting times. Tissue-engineered organs could be used to assist or even replace organs as a solution to the organ shortage.

Development of a tissue-engineered solid vital organ, such as a liver or kidney, is typically dependent on two main components—the parenchymal cells and a vascular network to supply oxygen and nutrients to the parenchymal cells. The diffusion distance of oxygen and nutrients from a blood vessel through tissue is very short (e.g., a few hundred microns). If cells, such as hepatocytes are grown in a three-dimensional scaffold and placed in the body near a capillary bed, only the cells in close proximity to the blood vessel will survive. Over time, new blood vessels may grow into the implanted cells, however, many of the cells that are far from the existing blood vessels will die without immediate blood supply.

Present designs for growing such cells provide a vascular network as a central part of the scaffold for a tissue-engineered, solid organ. The vascular network serves as the blood supply to deliver oxygen and nutrients to the other cells which are also placed in the scaffold to give the organ its function (e.g., hepatocytes for a tissue engineered liver). This approach allows a vascular network to be designed for the particular organ from the inlet vessels, which are anastomosed to the native circulation to the smallest vessels which perfuse the parenchymal cells. This tissue-engineered organ is implanted with blood vessels already adequately located in proximity to the parenchymal cells. This allows a thick, solid organ such as the liver, lung, heart, kidney, or other organs or tissues to be created and implanted.

In the body, blood vessels that supply organs typically enter the organs as one single vessel (typically an artery) and then branch in a pattern, reducing their diameter and greatly increasing their surface area until they form the smallest vessels known as capillaries. The capillaries supply the cells of the organ with oxygen and nutrients and remove waste products. From the capillaries, the vessels coalesce in a similar branching pattern to exit the organ often as a single vessel (typically a vein).

There is a need in the art for tissue-engineered organs having such a physiological vasculature network to provide sustained organ function following implantation. Therefore, it would be desirable to provide systems and methods for providing a tissue-engineered organ that has a structure similar to natural organs and is capable of similar performance for sufficient periods of time without malfunction.

SUMMARY

The present disclosure overcomes the aforementioned drawbacks by providing systems and methods that provide tissue-engineered organs that may be used to replace an organ, in vivo or ex vivo, assist an organ, temporarily replace an organ, and ascertain the efficacy and safety of a drug on human cells. The subject technology described herein includes the theory, concepts, design, manufacturing, testing, and applications of biomimetic vascular networks. These vascular networks have applications as a central part of a scaffold to create a tissue-engineered structure, such as an organ or other mammalian tissue. There are additional applications of this technology, for example, as a tool or a platform for drug discovery, development, and/or evaluation (e.g., toxicity, safety and/or efficacy) and as a platform for in vitro or in vivo research and testing.

More particularly, the present disclosure provides systems that include a tubular structure that puts organ tissue cells in communication with the vascular system such that the new cells receive nutrition and can communicate normally with other systems to support more sustained growth over a larger range.

In one configuration, a scaffold for tissue engineering is provided. The scaffold includes a vascular tube that defines a vascular diameter and is configured to receive vascular system seed cells, a non-vascular tube that defines a non-vascular tube diameter and is configured to receive organ system seed cells, and an opening formed between the vascular tube and the non-vascular tube and sized such that diffusion can occur but seeded cells are inhibited from migration between the vascular tube and the non-vascular tube.

In another configuration, a method is provided for populating a tubular structure including a vascular tube configured to receive vascular system seed cells, and an organ tissue tube configured to receive organ system seed cells. The method includes flowing hydrogel through the vascular tube in a first direction, flowing hydrogel through the organ tissue tube in a second direction opposite the first direction, introducing a chelating agent, forming a barrier between the vascular tube and the organ tissue tube while maintaining flow through the vascular tube and through the organ tissue tube, flushing the hydrogel from the vascular tube and the organ tissue tube while maintain the barrier intact, seeding the vascular tube with vascular system cells, and seeding the organ tissue tube with organ tissue cells.

In another configuration, another method is provided for populating a tubular structure including a vascular tube configured to receive vascular system seed cells, and an organ tissue tube configured to receive organ system seed cells. The method includes filling the organ tissue tube with hydrogel, maintaining the tubular structure at about thirty-seven degrees Celsius, seeding the vascular tube with vascular system cells, cooling the tubular structure to below about thirty-seven degrees Celsius, draining the hydrogel from the organ tissue tube while creating a barrier at the interface of the vascular tube and the organ tissue tube, and seeding the organ tissue tube with organ tissue cells.

These and other features and advantages of the present invention will become apparent upon reading the following detailed description when taken in conjunction with the drawings.

BRIEF DESCRIPTION OF THE DRAWINGS

FIG. 1 is a schematic illustration of a tubular structure according to one aspect of the present disclosure.

FIG. 2 is a cross-sectional, pictorial view of a liver.

FIG. 3 is a cross-sectional view of growing liver cells.

FIG. 4a is a cross sectional view of a tubular structure according to another aspect of the present disclosure.

FIG. 4b is a cross-sectional view of a tubular structure according to another aspect of the present disclosure.

FIG. 4c is a cross-sectional view of a tubular structure according to another aspect of the present disclosure.

FIG. 4d is a cross-sectional view of a tubular structure according to another aspect of the present disclosure.

FIG. 5 is a pictorial view of the tubular structure of FIG. 4a populated with living cells.

DETAILED DESCRIPTION

Figure 6:
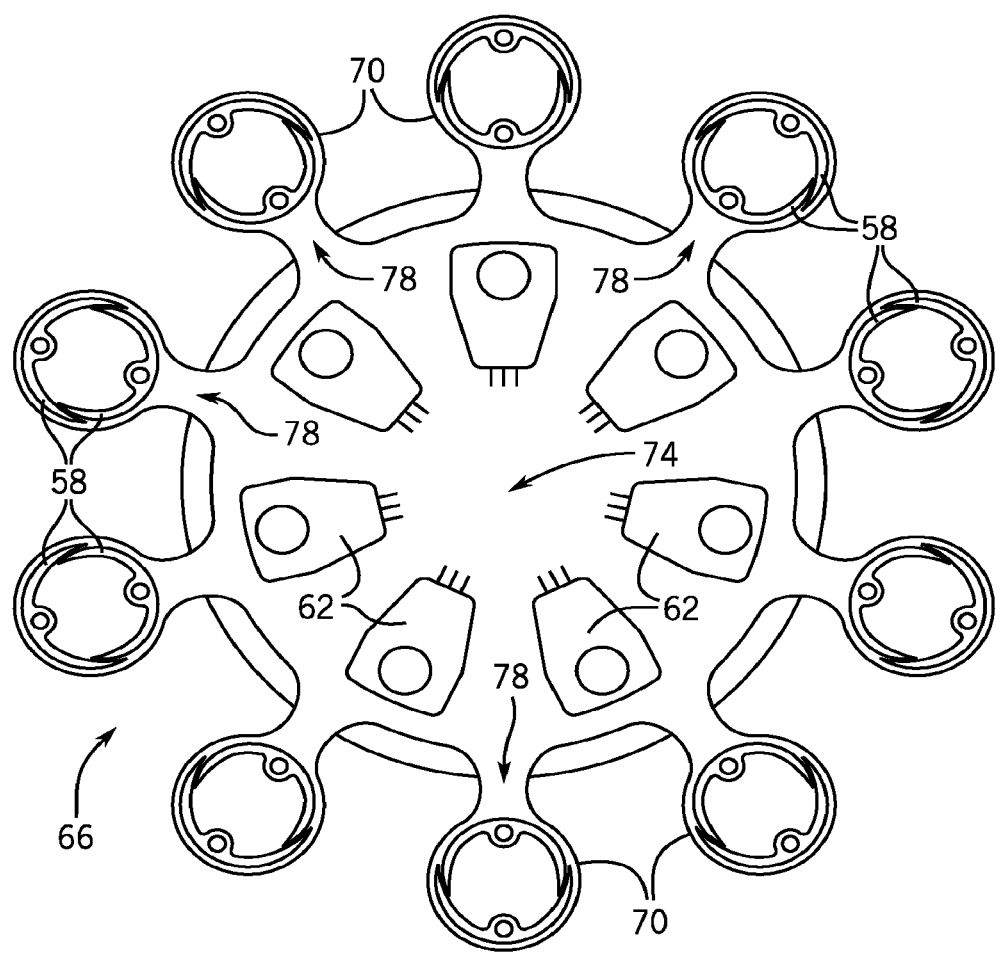
FIG. 6 a cross-sectional view of a tubular structure according to another aspect of the present disclosure.

The present disclosure provides systems and methods that overcome many of the prior-art challenges associated with tissue engineered vascular networks and artificial solid organs. The advantages, and other features of the technology disclosed herein, will become more readily apparent to those having ordinary skill in the art from the following detailed description of certain embodiments taken in conjunction with the drawings which set forth representative embodiments of the present invention and wherein like reference numerals identify similar structural elements.

It is to be understood that the subject technology is not intended to be limited to the particular constructs and methods discussed in the described embodiments, as one skilled in the art can extend the concepts involved using variations after reading the present disclosure. Although any methods and materials similar or equivalent to those described herein may be useful in the practice of the subject technology, certain compositions, films, methods and materials are described below. All relative descriptions herein such as top, bottom, left, right, up, and down are with reference to the Figures, and not meant in a limiting sense.

The process of creating an optimal vascular network design that performs sufficiently is aided by identifying and learning from the fundamental structure of blood vessels in the body. The vascular network of arteries, capillaries, and veins is complex. However, the basic structural principles can be utilized within the limits of currently-available manufacturing processes. There are several fundamental principles of blood vessels that have been utilized in the subject technology and incorporated into the design of the biomimetic vascular networks described herein. The concepts and the resulting designs are also advantageously refined using computational fluid dynamics (CFD) analysis. To this end, U.S. Pat. No. 8,591,597, issued on Nov. 26, 2013, is incorporated herein by reference in its entirety for all purposes.

FIG. 1 shows a tissue engineered tubular structure 14 that provides a liver structure leading from a large tube portion 18 to a capillary portion 22 through a branching structure. As with the above examples, the tissue engineered tubular structure 14 includes vascular tubes 26 and non-vascular tubes 30 arranged with a barrier 34 therebetween. The adjacency of the vascular tube 26 to the non-vascular tube 30 is maintained from the large tube portion 18, through the branching structure, to the capillary portion 22. The tubes 26, 30 are populated with living cells, so all the tubes, no matter their size, are nourished by the accompanying vascular tubes 26. The barrier 34 arranged between adjacent tubes 26, 30 allows for the passage of oxygen and nutrients while inhibiting cellular drift or movement within the scaffold. The arrangements discussed below with respect to FIGS. 4-9 show how different scaffolds/structures may be utilized to provide functional nourishment and communication between the vascular system and the biliary system.

FIG. 2 shows millions of tubular structures arranged within a liver 24. The tissue engineered tubular structure 14 aims to mimic the structures of the functioning liver 38. FIG. 3 shows a number of liver tissue cells forming in their tubular or ductular phase.

FIG. 4a shows a tubular structure 42 that includes a vascular tube 46 and a non-vascular tube 50 or, in this example, an organ tissue tube. In accordance with the non-limiting examples provided herein, the non-vascular tube 50 may be referred to as an organ tissue tube and, in the present, non-limiting example of engineering a liver, may be referred to as a biliary or bile tube 50. The vascular tube 46 is separated from the bile tube 50 by a barrier 54 that functions similarly to the Space of Disse in the liver 38. The barrier 54 shown in FIG. 4a is an open space formed between the vascular tube 46 and the bile tube 50 and is sized smaller than the minimum dimension of individual vascular or non-vascular cells such that seeded cells are maintained within the desired tube 46, 50, as discussed in further detail below.

The illustrated vascular tube 46 is a part of the capillary portion 22 and defines a diameter of about twenty microns (20 µm). The vascular tube 46 can define diameters up to about one centimeter (1 cm) upstream in the large tube portion 18.

The illustrated bile tube 50 is a part of the capillary portion 22 and defines a diameter of about fifty microns (50 µm). The bile tube 50 can define a diameter of up to about three centimeters (3 cm) in the large tube portion 18.

FIG. 4a shows the barrier 54 in the form of a space (e.g., a void, an opening, a gap, a slot, a passage, apertures, et cetera) defining a width of about two microns (2 µm). The barrier 54 can take on different dimensions. For example, FIG. 4b shows a barrier 54b in the form of a space defining a width of about four microns (4 µm). A barrier 54c, shown in FIG. 4c, is a space defining a width of about six microns (6 µm). A barrier 54d, shown in FIG. 4d, is a space defining a width of about eight microns (8 µm). The barriers 54 are exemplary, and those skilled in the art will recognize that other dimensions may be utilized while successfully practicing the disclosure. For example, significantly larger barriers, that is to say wider, may be utilized in arrangements where the barrier includes a membrane or other physical structure intended to limit mass transfer between the vascular tube 46 and the non-vascular bile tube 50.

FIG. 5 shows the tubular structure 42 populated with vascular system cells 58 and providing blood flow in a first direction A (into the page) and biliary system cells 62 providing bile flow in a second direction B (out of the page). In one configuration, the tubular structure 42 shown in FIG. 5 may be utilized to replace or assist a bile canaliculi portion or a bile ductule portion down stream of the Canal of Hering.

The barrier 54 is designed to maintain the vascular tube 46 spatially separate from the non-vascular or biliary tube 50, while providing communication between the vascular system and the non-vascular system. In other words, the barrier 54, may be a space as shown in FIGS. 4a-4d, or may be semi-permeable membrane with characteristics advantageously biomimetically designed, as a non-limiting example, based on the Space of Disse. Barriers that include a semi-permeable or temporary membrane will be discussed below with respect to FIGS. 7-9. Pore or opening sizes can vary, but are such that diffusion and gas and/or waste exchange can occur across the barrier 54.

A variety of tubular structures, even beyond the vascular 46 and non-vascular tubes 50 may be advantageously utilized to create an overall system or platform for tissue engineering. For example, FIG. 6 shows an additional tubular structure 66 that may be used to form a portion of the branching structure of, in this non-limiting example, the liver 38. The additional tubular structure 66 includes a plurality of capillary-type vascular tubes 70 that surround and nurture a larger biliary tube 74. A plurality of barriers 78 are arranged between each vascular tube 70 and the biliary tube 74. In the depicted configuration, ten vascular tubes 70 are utilized around a central biliary tube 74. In other configurations, more than ten or less than ten vascular tubes 70 may be included and may define a different relationship with the biliary tube 74. FIG. 6 again shows the tubular structure 66 populated with vascular system cells 58 and biliary system cells 62.

Figure 7:
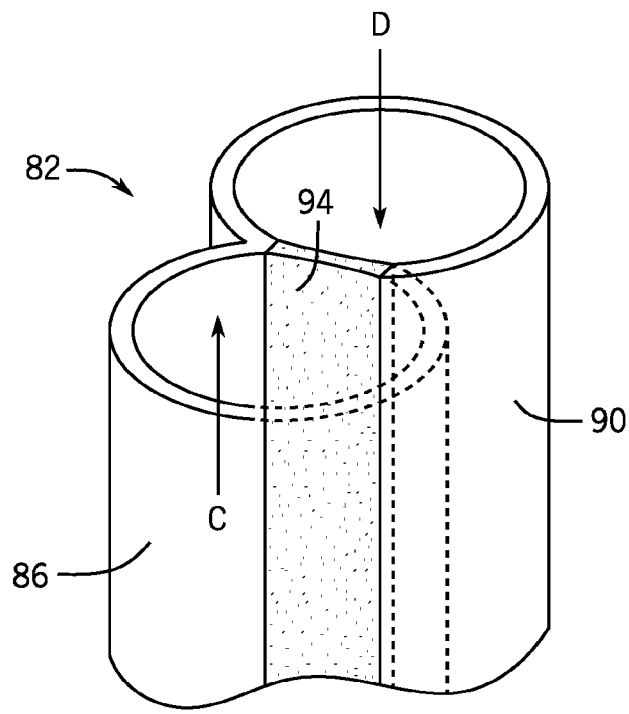
FIG. 7 is a pictorial view of a tubular structure according to another aspect of the disclosure.
Figure 8:
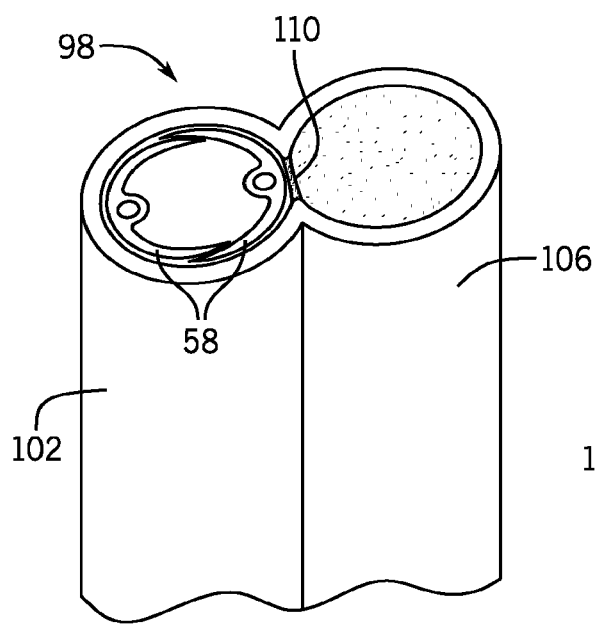
FIG. 8 is a pictorial view of a tubular structure according to another aspect of the disclosure.
Figure 9:
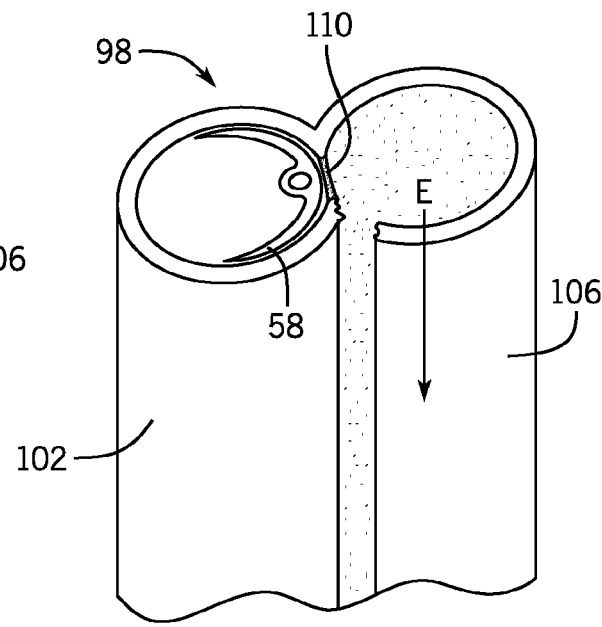
FIG. 9 is a pictorial view of a tubular structure according to another aspect of the disclosure.

FIGS. 7-9, discussed below, are directed to exemplary tubular structures and systems for loading the tubes with cells and keeping the cell populations separate during flow and cell loading. In particular, FIG. 7 shows a tubular structure 82 that includes a vascular tube 86, a biliary tube 90, and a barrier 94 arranged between the vascular tube 54 and the biliary tube 58. The barrier 94 is formed by flowing a hydrogel through the vascular tube 86 in a first direction C, and counterflowing a hydrogel through the biliary tube 90 in a second direction D. A chelating agent is then introduced which causes the hydrogel to form the barrier 94 at the interface between the vascular tube 86 and the biliary tube 90, while flow continues in the respective tubes. Once the barrier 94 is formed, vascular system cells 58 and biliary system cells 62 may be seeded.

FIGS. 8 and 9 show a tubular structure 98 that includes a vascular tube 102, a biliary tube 106, and a barrier 110. The barrier 110 may be formed by first filling the biliary tube 106 with a generally-solid hydrogel of collagen, for example, at thirty-seven degrees Celsius (37° C.). The vascular tube 102 is then seeded with vascular system cells 58. Once the vascular system cells 58 attach, the tubular structure 98 may then be cooled below thirty-seven degrees Celsius (37° C.) liquefying the hydrogel of collagen. The hydrogel of collagen can then be removed or flushed from the biliary tube 106, as illustrated by arrow E in FIG. 9, and biliary system cells 62 can be seeded.

In the configurations discussed above that include a physical barrier (e.g., those shown in FIGS. 7-9) the hydrogel or other material may be a temporary structure only in place during seeding and removed after the living cells are established, or the barrier material may remain in place after seeding, as desired.

Other hydrogels may be used, including pegs or gallium metal, for example. Some populations of cells may come from stem cell sources, especially from iPS cells. In one configuration, the vascular system cells 58 may be endothelial cells and the biliary system cells 62 may be hepatocytes or biliocytes.

The particular tubular structures discussed above provide barriers between the vascular tubes and the non-vascular tubes that define varying barrier widths. Additionally, the barriers may include a simple open space sized to spatially separate ethe biliary cells and the vascular cells, or may include a physical barrier. The vascular tubes and the non-vascular tubes may be arranged relative to one another to provide an interface or barrier width to provide desirable communication therebetween. The degree of communication will be proportional to the size of the barrier width. The above-described systems and methods can be modified to provide a barrier having a width between the full diameter of the tubes (i.e., the barrier width equals the vascular diameter or the non-vascular diameter) and zero (effectively cutting off communication between the vascular tube and the biliary tube in desired portions). In some configurations, the vascular diameter and the biliary diameter may be different.

Figure 10:
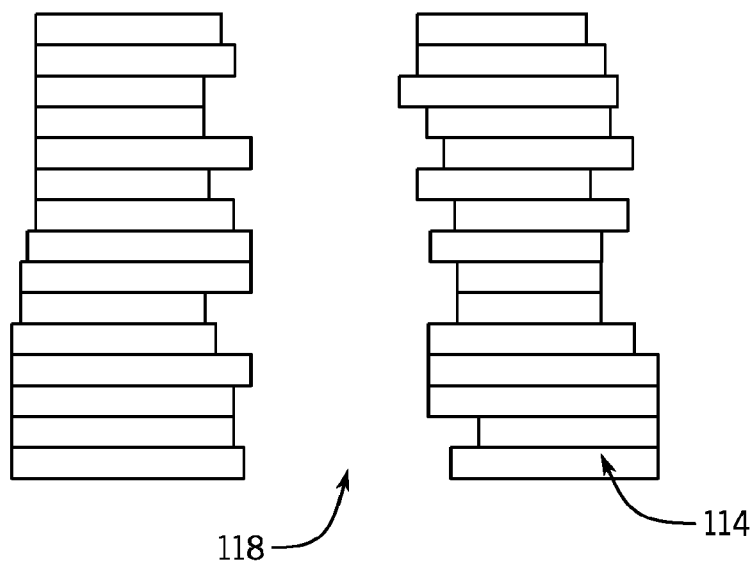
FIG. 10 is schematic representation of a tube produced using a 3D printer.

In one embodiment, the tubular structures discussed above may be constructed using 3D printing. For example, deposition 3D printing may be utilized to form hollow tubes in the desired structures and branching systems. 3D printing is an additive manufacturing process in which layers of material are deposited by a printer head as determined by a solid model or programmed geometry. 3D printing technology is rapidly developing and provides a construction method for creating very small parts with precise and accurate geometry from materials suitable for a variety of uses. In the present case, the tubular structures may be formed from suitable materials identified in the industry as successful for tissue engineering scaffold material. FIG. 10 represents how additive layers 114 may be printed to form a tube 118 on a very small scale. As shown in FIG. 10, on a small scale, manufacturing tolerances have a significant effect on the end product (e.g., the tube 118). Such inconsistencies in the manufacturing process will be more pronounced as the tube 118 gets smaller (e.g., in the capillary portions of the branching tissue engineered tubular structure 14 shown in FIG. 1). The effect shown in FIG. 10 may be referred to as jitter and creates a tube interior that is not perfectly smooth. Problems introduced by the 3D printing process, namely jitter, do not present catastrophic risks in this application because a rough side wall within vascular and organ tissue tubes is not undesirable.

Figure 11:
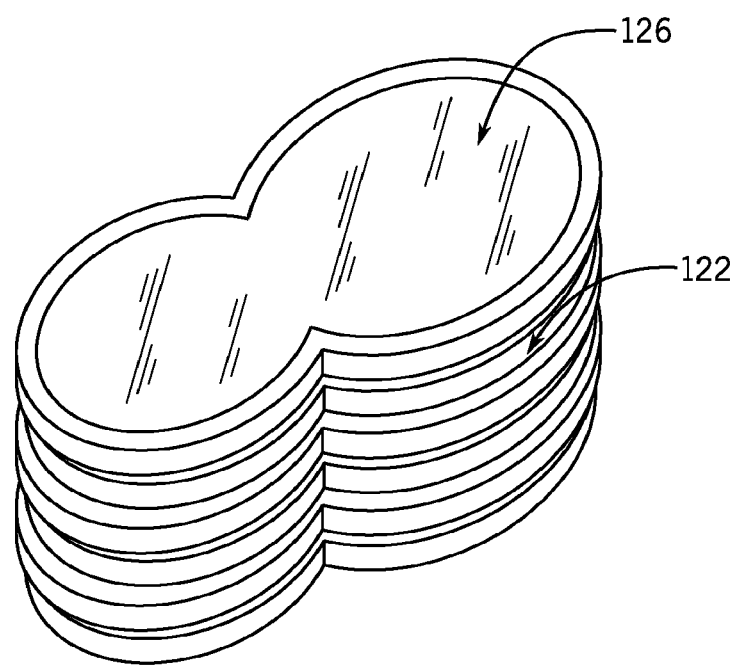
FIG. 11 is a schematic representation of an investment mold for a tube produced using 3D printing.

FIG. 11 represents an alternative method of utilizing 3D printing to construct the tubular structures discussed above. Layers 122 may be deposited and shaped to define the interior shape of a tube mold 126. The layers 122 are constructed of a material suitable for melting and used in an investment mold. To create the actual tubular structure desired, the tube mold 126 is housed in a mold cavity (not shown) and the desired material for the tubular structure is allowed to flow around the tube mold 126 and set. With the tubular structure set, the tube mold 126 is melted away leaving a finished and usable tubular structure. Again, the tolerances provided by the 3D printing process are inline with the needs and requirements of the above described disclosure.

In addition to the tubes, 3D printing may be used to form the barrier between the vascular and non-vascular tubes. For example, a temporary hydrogel barrier could be printed in place, thereby producing a ready to seed scaffold straight from the printer.

Thus, the above-described systems and methods provide examples of a structure that may be used to provide a larger tissue engineered sample that could be used to replace or assist failing organ tissue. The above configurations are described with reference to liver and biliary cells. However, the same concepts can be adapted to provide successful structures for other organ tissues, including the lungs and the like. Additionally, the concept of intercommunication between a vascular scaffold compartment and a non-vascular scaffold compartment may have uses beyond organ tissue applications. For example, facial transplantation could benefit from a scaffold structure that includes multiple non-vascular compartments interconnected selectively with one another and supported by one or more interconnected vascular compartments. For example, non-vascular compartments or structures in tubular or non-tubular configurations could include combinations of a bone compartment, a cartilage compartment, a muscle compartment, a nerve compartment, a soft tissue compartment, a skin compartment, et cetera. These compartments could be arranged with barriers therebetween to allow the desired amount or type of communication. The one or more vascular compartments could be arranged to provide nutrient exchange with the non-vascular compartments to support growth and healthy living cells once established.

Such complex tissue engineered structures can be based on a CT scan of a patient and constructed using a 3D printer to match the patients natural structure. The printed scaffold can then be seeded with the appropriately signaled stem cells. With proper geometry and construction, all vital organs and complex tissues can be built this way.

The present invention has been described in terms of one or more preferred embodiments, and it should be appreciated that many equivalents, alternatives, variations, and modifications, aside from those expressly stated, are possible and within the scope of the invention.

I claim:

1. A device configured as an artificial organ, the device comprising:
    a scaffold structure comprising a branching structure comprising
    a plurality of vascular compartments;
    a plurality of non-vascular compartments, wherein
        a portion of the plurality of vascular compartments and a portion of the plurality of non-vascular compartments are monolithic,
        each non-vascular compartment in the plurality of non-vascular compartments shares a one-to-many relationship with a respective vascular compartment in the plurality of vascular compartments, and
        the portion of the plurality of vascular compartments and the portion of the plurality of non-vascular compartments are configured to each other to provide an interface between the portion of the plurality of vascular compartments and the plurality of non-vascular compartments; and
    a barrier formed at the interface between the portion of the plurality of vascular compartments and the portion of the plurality of non-vascular compartments, wherein the barrier comprises a characteristic dimension configured to allow a degree of fluidic communication between the portion of the plurality of vascular compartments and the portion of the plurality of non-vascular compartments.

2. The device of claim 1, wherein the characteristic dimension of the barrier is less than a characteristic dimension of a respective vascular compartment in the plurality of vascular compartments or a characteristic dimension of a respective non-vascular compartment in the plurality of non-vascular compartments.

3. The device of claim 1, wherein the barrier comprises hydrogel.

4. The device of claim 3, wherein the hydrogel comprises collagen.

5. The device of claim 3, wherein the hydrogel comprises polyethylene glycol (PEG).

6. The device of claim 1, wherein a characteristic dimension of a respective vascular compartment in the plurality of vascular compartments is different from a characteristic dimension of a respective non-vascular compartment in the plurality of non-vascular compartments.

7. The device of claim 1, wherein the barrier comprises a semi-permeable membrane.

8. The device of claim 1, wherein the scaffold structure is configured to support flow of a first medium through the plurality of vascular compartments in a first direction and flow of a second medium through the plurality of non-vascular compartments in a second direction.

9. The device of claim 8, wherein the first direction is opposite the second direction.

10. The device of claim 1, wherein the scaffold structure comprises a resorbable material or a biodegradable material.

11. The device of claim 1, wherein the barrier comprises a resorbable material or a biodegradable material.

12. The device of claim 1, wherein the barrier comprises an opening, and the characteristic dimension of the barrier is a size of the opening.

13. The device of claim 1, wherein:
    a characteristic dimension of a respective vascular compartment in the plurality of vascular compartments is from about 20 microns ($\mu m$) to about 1 centimeter (cm); and
    a characteristic dimension of a respective non-vascular compartment in the plurality of non-vascular compartments is from about 50 $\mu m$ to about 3 cm.

14. The device of claim 1, wherein the characteristic dimension of the barrier is from about two $\mu m$ to about eight $\mu m$.

15. The device of claim 1, wherein the plurality of non-vascular compartments and the plurality of vascular compartments collectively comprise at least a million compartments.

16. The device of claim 1, further comprising a plurality of barriers formed at the interface between the plurality of vascular compartments and the plurality of non-vascular compartments.

17. The device of claim 1, wherein the barrier is monolithic.

18. The device of claim 1, wherein a vascular compartment in the plurality of vascular compartments and a non-vascular compartment in the plurality of non-vascular compartments are each non-tubular.

* * * * *